United States Patent
Pettis et al.

(10) Patent No.: US 10,900,876 B2
(45) Date of Patent: Jan. 26, 2021

(54) METHODS AND DEVICES FOR PRODUCING CELLULAR SUSPENSIONS FROM TISSUE SAMPLES

(71) Applicant: Becton, Dickinson and Company, Franklin Lakes, NJ (US)

(72) Inventors: Ronald J. Pettis, Cary, NC (US); Mitchell Ferguson, Clayton, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 161 days.

(21) Appl. No.: 16/082,513

(22) PCT Filed: Mar. 7, 2017

(86) PCT No.: PCT/US2017/021207
§ 371 (c)(1),
(2) Date: Sep. 5, 2018

(87) PCT Pub. No.: WO2017/156036
PCT Pub. Date: Sep. 14, 2017

(65) Prior Publication Data
US 2019/0017908 A1     Jan. 17, 2019

Related U.S. Application Data (60) Provisional application No. 62/306,576, filed on Mar. 10, 2016.

(51) Int. Cl.
| | |
|---|---|
| *G01N 1/38* | (2006.01) |
| *B01F 11/02* | (2006.01) |
| *C12M 1/33* | (2006.01) |
| *G01N 1/28* | (2006.01) |
| *G01N 15/14* | (2006.01) |
| *G01N 15/10* | (2006.01) |

(52) U.S. Cl.
CPC ............... *G01N 1/38* (2013.01); *B01F 11/02* (2013.01); *C12M 45/02* (2013.01); *G01N 1/286* (2013.01); *G01N 15/1459* (2013.01); *B01F 2215/0037* (2013.01); *B01F 2215/0073* (2013.01); *G01N 2001/2866* (2013.01); *G01N 2001/386* (2013.01); *G01N 2015/1006* (2013.01)

(58) Field of Classification Search
CPC ...... G01N 1/38; G01N 1/286; G01N 15/1459; G01N 2001/2866; G01N 2001/386; G01N 2015/1006; C12M 45/02; B01F 11/02; B01F 2215/0037; B01F 2215/0073
See application file for complete search history.

(56) References Cited

U.S. PATENT DOCUMENTS

| | | | |
|---|---|---|---|
| 5,030,002 A | 7/1991 | North | |
| 7,497,119 B2 | 3/2009 | Brooks et al. | |
| 8,778,414 B2 * | 7/2014 | Warlick | A23F 3/18 424/725 |
| 2015/0174511 A1 | 6/2015 | Curran et al. | |
| 2015/0177111 A1 | 6/2015 | Warner et al. | |

FOREIGN PATENT DOCUMENTS

WO    WO/2015/061448 A2    10/2014

OTHER PUBLICATIONS

Donnenberg et al., International Drug Discovery, 2011, p. 1-3.*
Chandler et al., Analytical Biochemistry, 2003, vol. 312, p. 182-190.*
(resodynmixers.com) LabRAM Mixer Family; Webpage [online]; Jul. 25, 2014; retrieved on Sep. 6, 2018, Retrieved from the Internet: <URL:http://resodynmixers.com/>, 2 pages.

* cited by examiner

*Primary Examiner* — Kade Ariani
(74) *Attorney, Agent, or Firm* — Kathleen Y. Rao; Bret E. Field; Bozicevic, Field & Francis LLP (57) ABSTRACT

Aspects of the present disclosure include methods of producing a cellular suspension from a tissue sample by applying resonant acoustic energy to a container comprising the tissue sample in a manner sufficient to produce a cellular suspension from the tissue sample. Resonant acoustic mixers and kits for use in producing a cellular suspension from a tissue sample are also provided.

12 Claims, 5 Drawing Sheets

METHODS AND DEVICES FOR PRODUCING CELLULAR SUSPENSIONS FROM TISSUE SAMPLES

CROSS-REFERENCE TO RELATED APPLICATION

Pursuant to 35 U.S.C. § 119(e), this application claims priority to the filing date of U.S. Provisional Patent Application No. 62/306,576, filed Mar. 10, 2016; the disclosure of which application is herein incorporated by reference.

INTRODUCTION

The current clinical gold standard for characterizing solid tumors and stratifying patients relies partially on analyzing formalin-fixed paraffin-embedded (FFPE) tumor slices via immunohistochemistry (IHC), but the thin 5-7 micron ($\mu$) sections represent less than 0.01% of the total cell population in a typical tumor biopsy and therefore not a thorough representation of a tumor's composition. More specific diagnoses, which will ultimately lead to better patient outcomes, will require clinicians to adopt new, more comprehensive methods of solid tumor analysis.

One of the newest methods on the forefront of cancer microenvironment and solid tumor research involves dissociating solid tumors into single cell suspensions and subsequently characterizing subpopulations of the tumor using cell surface markers and flow cytometric analysis. This type of "deep phenotyping" is critical to better understand which tumor subpopulations are deleterious, which subpopulations are benign and the complex mechanisms through which these populations interact, evolve and evade therapeutic intervention.

A key aspect of this workflow is rendering a heterogeneous solid tumor biopsy into a complete single cell suspension without significantly altering surface marker expression or discriminately affecting cell viability. This is typically performed using a combination of mechanical, enzymatic, and/or temperature incubation treatments. These methods are time-intensive, inefficient, and highly subjective as the skill and experience of the researcher can be a factor.

SUMMARY

Aspects of the present disclosure include methods of producing a cellular suspension from a tissue sample by applying resonant acoustic energy to a container that includes the tissue sample in a manner sufficient to produce a cellular suspension from the tissue sample. Additional aspects include resonant acoustic mixers that have a mixing container, a resonant acoustic energy source operatively coupled to the mixing container, and a tissue sample present in the mixing container. Kits for use in producing a cellular suspension from a tissue sample are also provided, where such kits include an enzymatic dissolution agent and a milling agent.

BRIEF DESCRIPTION OF THE FIGURES

The invention may be best understood from the following detailed description when read in conjunction with the accompanying drawings. Included in the drawings are the following figures.

DETAILED DESCRIPTION

Aspects of the present disclosure include methods of producing a cellular suspension from a tissue sample by applying resonant acoustic energy to a container that includes the tissue sample in a manner sufficient to produce a cellular suspension from the tissue sample. Additional aspects include resonant acoustic mixers that have a mixing container, a resonant acoustic energy source operatively coupled to the mixing container, and a tissue sample present in the mixing container. Kits for use in producing a cellular suspension from a tissue sample are also provided, where such kits include an enzymatic dissolution agent and a milling agent.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Methods of the present disclosure are based on the finding that applying resonant acoustic energy to a container with a solid tissue sample therein can produce a cellular suspension containing viable cells. As described below, these viable cell suspensions find use in numerous downstream assays and analyses.

Resonant acoustic energy can be supplied to the container, with the tissue sample therein, using any convenient protocol. In some instances, resonant acoustic energy may be supplied by cyclic linear displacement of the container. In systems where fluid motion is driven by resonant acoustic energy, motion may be imparted substantially uniformly throughout all volume elements of the container providing lower velocity gradients within the tissue sample in the container. Although it will be appreciated that numerous mechanical or electronic transducer arrangements can be utilized to supply the cyclic linear displacement, one example of commercially available equipment suitable for supplying the necessary acoustic energy is the Resodyn™ LabRAM I acoustic mixer (Resodyn Acoustic Mixers, Inc.; see FIG. 1). This technology has been described, for example, in U.S. Pat. No. 7,188,993 to Howe et al., and employs linear displacement to introduce a standing linear acoustic wave into a medium, for example, gas, liquid or solid, residing within a container affixed to the device. The disclosure of U.S. Pat. No. 7,188,993 is incorporated herein by reference.

In certain embodiments, the method includes placing a solid tissue sample into a container, e.g., in an aqueous buffer or other suitable medium, and subjecting the tissue to resonant acoustic energy of sufficient frequency and amplitude, and for a sufficiently sustained period of time, to produce a cellular suspension containing viable cells derived from the solid tissue. As the term is used herein, resonant acoustic energy (or simply acoustic energy) is linear or spherical energy propagation through a tangible medium which is within the frequency range of 10 hertz to 20,000 Hertz (Hz). It will be appreciated that in methods of the present disclosure the exact frequency may be selected by a user to provide a standing wave in the solid tissue sample from which a cell suspension is being produced. The frequency required to achieve a standing wave may vary depending upon the nature of the solid tissue, the liquid (e.g., buffer or media) in which the solid tissue is suspended, the amount of buffer employed, the dimensions of the container in which the tissue sample is held (and to which the resonant acoustic energy is applied), etc. In embodiments of the methods of the present invention, resonant acoustic energy at a frequency of from 10 Hz up to 100 Hz is employed, including from 30 to 90 Hz, from 50 to 70 Hz, e.g., 60 Hz. In certain embodiments, the acoustic energy is applied to the tissue sample in the container from 50 to 150 g of acceleration (where "g" is the force of gravity), including from 70 to 120 g, e.g., 100 g. The amplitude of the applied resonant acoustic energy and duration that the resonant acoustic energy is applied may also vary as desired.

The solid tissue being dissociated in the methods disclosed herein can be any solid tissue of interest to a user, including normal tissue and/or diseased tissue from a subject, e.g., a tumor biopsy sample, tumor tissue, inflamed or infected tissue, cadaveric tissue, etc. In certain embodiments, the subject from which the tissue is derived is a mammal, e.g., a human. In some embodiments, the method includes obtaining the tissue directly from a subject whereas in other embodiments the tissue is received from a third party. Examples of tissues/biopsies include gastrointestinal tract tissue (e.g., esophagus, stomach, duodenum, colon and terminal ileum), lung, liver, vascular (e.g., veins, arteries, lymph vessels, lymph node), spleen, thymus, muscle, integumentary tissue (e.g. skin, subcutis, exocrine glands), endocrine (e.g., pancreas, pituitary, hypothalamus, thyroid, parathyroid, adrenal, thymus, gonads) nervous system (e.g., brain, nerve, and meningeal tissue), prostate (e.g., transrectal biopsy and/or transurethral biopsy), urogenital system tissue (e.g., renal biopsy, endometrial biopsy and cervical conization), breast tissue, etc. Such tissue/biopsy tissue can be harvested according to any convenient method, including punch biopsy, surgical methods, endoscopy-enabled methods, needle core biopsy methods, etc. In certain embodiments, the tissue is a normal tissue or diseased tissue grown in vitro, e.g., an embryoid body or other differentiated tissue (e.g., muscle tissue). No limitation in this regard is intended. The initial mass of the tissue sample may vary as desired.

In certain embodiments, the tissue being dissociated is not subjected to any additional tissue dissociating treatment or agent prior to or during application of the resonant acoustic energy. In other embodiments, the tissue being dissociated is subjected to an additional tissue dissociating treatment or agent prior to or during, or after application of the resonant acoustic energy, e.g., physical processing (e.g., mincing, crushing, and the like), the inclusion of milling agents (e.g., beads), the enzymatic treatment and/or chemical treatment (e.g., hyaluronidases, collagenases, DNAses, proteases, chelating agents (e.g., ethylenediaminetetraacetic acid, or EDTA)). Thus, in certain embodiments the tissue sample is contacted with an enzyme/chemical prior to and/or during applying acoustic resonant energy. For example, the container in which the tissue sample is placed can include an enzymatic dissolution agent. In other embodiments, the container includes a milling agent or milling media, e.g., polymeric beads.

For carrying out the method of the present disclosure, any convenient, sealable container may be employed. Examples of containers of interest include those that can be fixed to a carriage of the acoustic mixing equipment utilized to prepare the cell suspension. Examples of suitable containers include, but are not limited to, a sealable bottle, tube (e.g., a conical tube) or flask of any material (e.g., glass, plastic or metal), a sealable plastic bag, and a sealable micro-titer multiple well plate. In certain embodiments, the container has a volume ranging from 100 µL to 500 mL, including from 1 mL to 250 mL, from 5 mL to 100 mL, and anywhere in between.

Once the tissue in the container has been subjected to the acoustic resonant energy, the acoustic energy-processed sample can be subjected to any of a variety of clean-up or separation steps to obtain a sample comprising live dissociated cells in a cellular suspension. The clean-up/separation steps employed are generally based on the specific method used to dissociate the tissue and the desired form of the cellular suspension. For example, where a milling agent is used, the method can further include separating the milling agent from the acoustic energy-processed sample (e.g., via sieving or filtration, magnetic separation, flotation, density centrifugation). Where enzyme and/or chemical dissociation agents are employed, the acoustic energy-processed sample can be washed with buffer or media to remove the dissociation agent, or the agent can otherwise be inactivated in solution. In addition, non-cellular debris and/or non-viable cells can be removed from the acoustic energy-processed sample. Any convenient separation technique may be employed in these clean-up/separation steps, including decantation, filtering/size exclusion separation, centrifugation (e.g., density gradient centrifugation), or combinations thereof (e.g., centrifuging through a properly sized sieve/mesh).

The above described steps result in the production of a cellular suspension from an initial tissue sample. Cellular suspensions produced by methods of the invention may be characterized as being liquid compositions in which cells are dissociated from each other, such that they freely move relative to each other in the liquid composition. In cellular suspensions produced by embodiments of the invention, the number % of cells that are present as single cells in the suspension (i.e., not stably associated with one or more other cells) may vary, and in certain instances is 60% or more, such as 70% or more, including 80% or more, such as 90% or more, 95% or more, up to 100%. In some cases the interstitial cellular fluids isolated from these cellular suspensions may also be of interest for further manipulation or analysis. In such instances, methods may include isolating such fluids and, optionally manipulating or analyzing such fluids, as desired.

Once a cellular suspension has been obtained, the cellular suspension can be manipulated and/or analyzed as desired by the user. Non-limiting examples include manipulations and/or analyses related to: protein analysis (e.g., western blotting, ELISAs, cell surface marker analysis/sorting, intracellular protein expression, etc.), nucleic acid analysis (e.g., gene expression level detection, genome and exome sequence analyses, etc.), determining cellular growth/differentiation properties in vitro and/or in vivo (e.g., in a transplantation setting, in an in vitro differentiation assay, etc.), quantifying cellular types and subtypes and their relative percentages within a sample, identifying therapeutically useful cells (e.g., tumor infiltrating lymphocytes (TILs)), identifying and/or purifying stem/progenitor cell populations, diagnosing a disease, staging disease progression, determining the best course of therapy for a disease/condition in a subject, etc. Similar analyses can be utilized with interstitial fluids obtained from the separated cell-free solution.

In certain embodiments, the cells in the cell suspension are manipulated and/or analyzed using antibodies (or other affinity reagents) that are specific for expression products of interest. For example, antibodies that bind to a specific cell surface marker can be used to purify, isolate or enrich for cells that express the marker (or multiple different markers). In one embodiment, one or more marker-specific antibody can be coupled to a solid support, e.g., polymeric or magnetic beads, a tissue culture plate, a slide, etc., to form an affinity surface to which only cells recognized by the antibodies can adhere. After non-adherent cells are washed away, the bound cells can then recovered by any convenient method, e.g., by gentle shaking, by treatment with protease, by flushing with an excess of the peptide containing the epitope for the antibody, etc.

In certain embodiments, the cells can be separated using antibodies coupled to a detectable label (e.g., a fluorescent dye) by fluorescence activated cells sorting (FACS). Thus, in certain embodiments, manipulating the cell suspension includes sorting one or more subset(s) of cells from the cellular suspension by FACS. While flow cytometers find use in sorting cells from cell suspensions, flow cytometry also can be used as a purely analytical tool (and thus the cells analyzed are not sorted for further processing). Therefore, in certain embodiments, the cells are analyzed for the presence or absence of one or more gene expression products by flow cytometry. Gene expression products include both extracellular and intracellular gene expression products and include peptides, proteins, glycoproteins, ribonucleic acids (RNAs, e.g., mRNA, microRNA, etc.), and the like. Where nucleic acids are analyzed by flow cytometry, a label, such as a dye, specific for nucleic acids can be employed to determine the total nucleic acid content or an affinity reagent suitable to label specific cells containing nucleic acids of a particular sequence. The affinity reagent employed can be a detectably labeled nucleic acid probe that include a sequence that can bind specifically to its desired target sequence under moderate to high stringency hybridization conditions. For example, the nucleic acid probe can include a nucleic acid sequence that is complementary (or substantially complementary) to a target nucleic acid sequence that is at least 15 nucleotides in length, e.g., at least 20, at least 25, at least 30, at least 50, at least 100, etc., nucleotides in length. The design and use of nucleic acid probes that are specific for a target of interest can be done using any convenient protocol.

In certain embodiments, non-viable cells in the cell suspension can be identified and/or selected against, either in sorting or purely analytical assays, by employing dyes associated with dead cells (e.g., propidium iodide, 7-AAD, trypan blue, etc.). Any technique or vital may be employed which is not unduly detrimental to the viability of the selected cells may be employed.

Compositions and Kits

Aspects of the present disclosure include a resonant acoustic mixer that finds use in the tissue dissociation methods described above, where the mixer includes: a mixing container; a resonant acoustic energy source operatively coupled to the mixing container; and a tissue sample present in the mixing container.

Resonant acoustic mixers that find use in the present composition include an energy source that can supply cyclic linear displacement to a mixing container with a tissue sample present therein. The resonant acoustic energy supplied to the mixing container in such resonant acoustic mixers is of sufficient frequency and amplitude, and can be provided for a sufficiently sustained period of time, to produce a cellular suspension containing viable cells derived from the solid tissue in the container. The resonant acoustic mixer is capable of providing resonant acoustic energy to the mixing container within a frequency range of from 10 Hz to 100 Hz, including from 30 to 90 Hz, from 50 to 70 Hz, e.g., 60 Hz, and at an acceleration of from 50 to 150 g, including from 70 to 120 g, e.g., 100 g.

Figure 1:
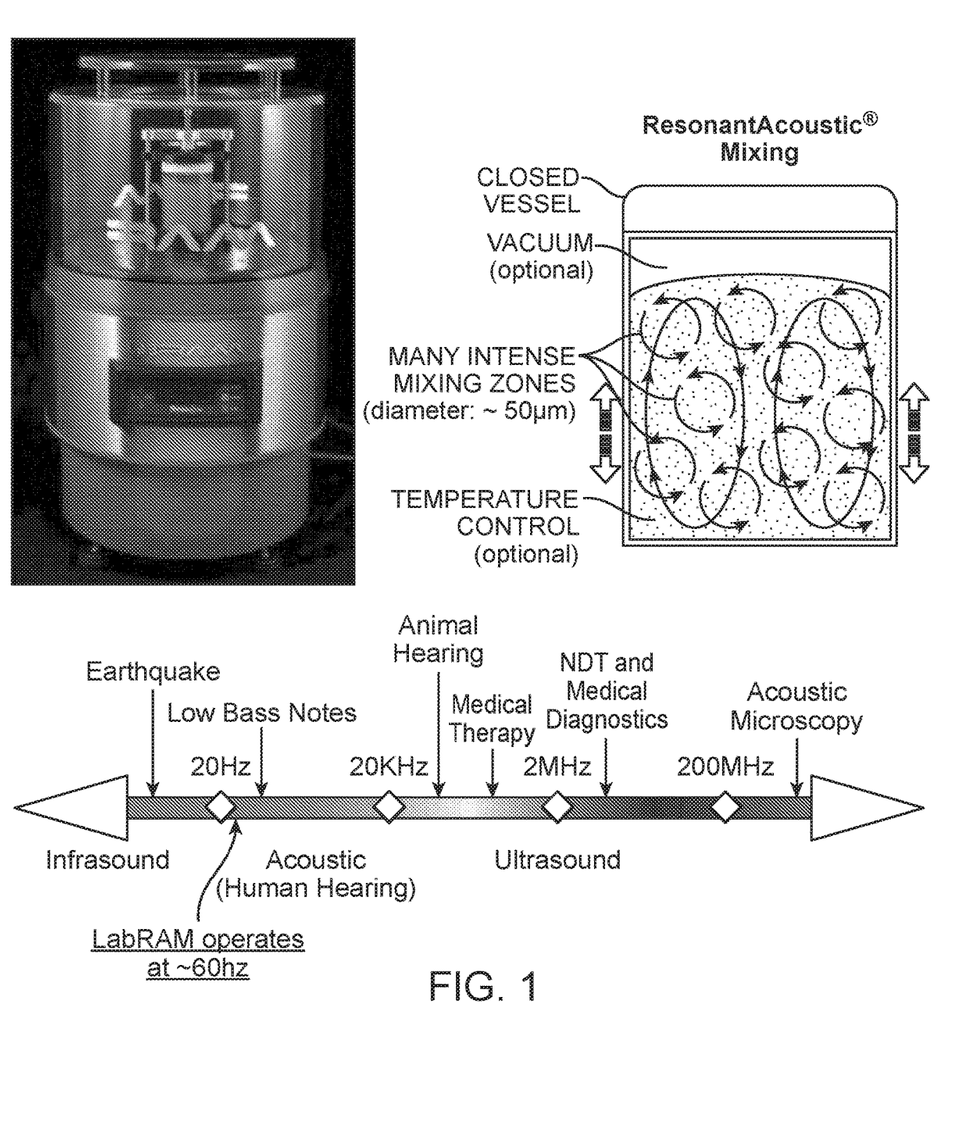
FIG. 1 shows the LabRAM I acoustic mixer employed in the Examples described herein. The LabRAM I (top left photograph) uses low frequency, high intensity acoustic energy to create a uniform shear field throughout the mixing vessel. A cartoon showing the mixing vessel (top right) indicates the many intense mixing zones (red circular arrows) produce with the application of the acoustic energy that are approximately 50$\mu$ in diameter. The temperature of the vessel and the precise frequency and duration of the acoustic energy applied can be controlled as desired by a user. The diagram at the bottom of FIG. 1 shows a spectrum of acoustic frequencies and indicates where on this spectrum the LabRAM I acoustic mixing device operates (i.e., at approximately 60 Hertz (Hz)).

As noted above, one example of a commercially available equipment suitable for supplying the necessary acoustic energy is the Resodyn™ LabRAM I acoustic mixer (Resodyn Acoustic Mixers, Inc.; see FIG. 1). This technology has been described, for example, in U.S. Pat. No. 7,188,993 to Howe et al., (the disclosure of which is herein incorporated by reference) and employs linear displacement to introduce a standing linear acoustic wave into a medium, for example, gas, liquid or solid, residing within a container affixed to the device.

The tissue sample in the mixing container can be any solid tissue of interest to a user, including normal tissue and/or diseased tissue from a subject, e.g., a tumor biopsy sample, tumor tissue, inflamed or infected tissue, cadaveric tissue, etc. In certain embodiments, the subject from which the tissue is derived is a mammal, e.g., a human. In some embodiments, the method includes obtaining the tissue directly from a subject whereas in other embodiments the tissue is received from a third party. Examples of tissues/biopsies include gastrointestinal tract tissue (e.g., esophagus, stomach, duodenum, colon and terminal ileum), lung, liver, vascular (e.g., veins, arteries, lymph vessels, lymph node), spleen, thymus, muscle, integumentary tissue (e.g. skin, subcutis, exocrine glands), endocrine (e.g., pancreas, pituitary, hypothalamus, thyroid, parathyroid, adrenal, thymus, gonads) nervous system (e.g., brain, nerve, and meningeal tissue), prostate (e.g., transrectal biopsy and/or transurethral biopsy), urogenital system tissue (e.g., renal biopsy, endometrial biopsy and cervical conization), breast tissue, etc. Such tissue/biopsy tissue can be harvested according to any convenient method, including punch biopsy, surgical methods, endoscopy-enabled methods, needle core biopsy methods, etc.

In certain embodiments, the tissue is a normal tissue or diseased tissue grown in vitro, e.g., an embryoid body or other differentiated tissue (e.g., muscle tissue). No limitation in this regard is intended.

In certain embodiments, the mixing container further includes an agent or agents that aid in the tissue dissolution process, e.g., an enzymatic or chemical dissolution agent(s) and/or a milling agent. Such agents include, but are not limited to: hyaluronidases, collagenases, DNAses, proteases, chelating agents (e.g., ethylenediaminetetraacetic acid, or EDTA), and beads.

The mixing container can be any convenient sealable container which can be fixed to the carriage of the resonant acoustic mixing device. Examples of suitable containers include, but are not limited to, a sealable bottle, tube (e.g., a conical tube) or flask of any material (e.g., glass, plastic or metal), a sealable plastic bag, and a sealable micro-titer multiple well plate. In certain embodiments, the container has a volume ranging from 100 μL to 500 mL, including from 1 mL to 250 mL, from 5 mL to 100 mL, and anywhere in between.

In certain embodiments, the resonant acoustic mixer is operatively coupled to a device or component that finds use in downstream manipulation or analysis of the acoustic energy-processed tissue sample. In certain embodiments, the device or component is configured to perform any of a variety of clean-up or separation steps to obtain a sample comprising live dissociated cells in a cellular suspension, e.g., an automated cell enrichment/purification system. Examples include, but are not limited to, a magnetic activated cell sorter (e.g., MACS system, Miltenyi Biotec), flow cytometer/cell sorters, or both.

Flow cytometer systems of interest include flow cell nozzles and optics subsystems for detecting light emitted by a sample in a flow stream. Suitable flow cytometer systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5): 502-11; Alison, et al. *J Pathol*, 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter, BD Biosciences FACSVerse™, BD Accuri™ C6, BD FACSCelesta™, BD LSRFortessa™, BD Biosciences FACSCanto™ II, BD LSRFortessa™ X-20, etc. or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040;

5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Also provided by the subject disclosure are kits and systems for practicing the subject methods, as described above, e.g., for producing a cellular suspension from a tissue sample by applying resonant acoustic energy. In certain embodiments, the kit includes one or more of: an enzymatic dissolution agent, a chemical dissolution agent, and a milling agent. Enzymatic/chemical dissolution agents include, but are not limited to hyaluronidases, collagenases, DNAses, proteases, EDTA, and the like; and milling agents include beads, e.g., polymeric beads.

In some embodiments, the kit includes a sealable mixing container that is configured to hold a solid tissue sample and be attached/fixed to the carriage of an acoustic mixing device (as described above). Examples of suitable containers include, but are not limited to, a sealable bottle, tube (e.g., a conical tube) or flask of any material (e.g., glass, plastic or metal), a sealable plastic bag, and a sealable micro-titer multiple well plate. In certain embodiments, the container has a volume ranging from 100 µL (e.g., for each well of a 96 well plate) to 500 mL, including from 1 mL to 250 mL, from 5 mL to 100 mL, and anywhere in between.

The subject systems and kits may also include one or more other reagents for preparing or processing a tissue sample according to the subject methods. The reagents may include one or more sample preparation devices (e.g., scalpels, syringes, etc.), reagents and/or buffers, sieves, filters, additional enzymatic reagents, affinity reagents (e.g., antibodies), etc. As such, the kits may include one or more containers such as vials or bottles, with each container containing a separate component for carrying out a tissue sample processing or preparing step and/or for carrying out solid tissue dissolution using resonant acoustic energy as described herein. It is noted that the various components of the kits may be present in separate containers or certain compatible components may be pre-combined into a single container, as desired.

In addition to above-mentioned components, the subject kits typically further include instructions for using the components of the kit to practice the subject methods, e.g., to prepare a cell suspension from a solid tissue sample as described herein. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

In the experiments described below, the use of low frequency, high intensity acoustic energy for dissociating solid tissues was evaluated under a series of different conditions. The results demonstrate that acoustic energy can be used to completely dissociate tissues, even without manual mincing or enzyme treatments, while maintaining equivalent cell yields and viabilities as compared to other standard protocols.

The LabRAM I from Resodyn™ Acoustic Mixers, Inc. (Butte, Mont.) system was employed. The LabRAM I is a lab mixer that thoroughly mixes gases, liquids, solids, powders and very viscous compounds with a nominal capacity of 1 pint. A variety of mixing vessels may be used including small vials and disposable plastic containers and bags. The LabRAM I uses low frequency, high intensity acoustic energy to create a uniform shear field throughout the mixing vessel (see FIG. 1). The result is rapid fluidization (like a fluidized bed) and dispersion of material. ResonantAcoustic® Mixing differs from ultrasonic mixing in that the frequency of acoustic energy is orders of magnitude lower than ultrasonic energy (see frequency scale in FIG. 1). As a result, the scale of mixing is larger. Unlike impeller agitation, which mixes by inducing bulk flow, the mixing in an acoustic mixer occurs on a microscale throughout the mixing volume. Resonant Acoustic® Mixing introduces acoustic energy into liquids, slurries, powders and pastes. An oscillating mechanical driver creates motion in a mechanical system comprised of engineered plates, eccentric weights and springs. This energy is then acoustically transferred to the material to be mixed. The underlying technology principle is that the system operates at resonance. In this mode, there is a nearly complete exchange of energy between the mass elements and the spring elements in the mechanical system. In a Resonant Acoustic® Mixer, the only element that absorbs energy (apart from some negligible friction losses) is the mix load itself. Thus, the ResonantAcoustic®Mixer provides a highly efficient way of transferring mechanical energy directly into the mixing materials. As an example, a Resonant Acoustic® Mixer using 40 HP would require over 770 HP in a non-resonant equipment configuration to mix the same load.

Example 1

Experimental Design and Controls

The experiments described in this section were performed using mouse kidney and liver tissue. Each experiment utilized a positive control consisting of a matched piece of organ tissue processed using a Standard Protocol (Table 1). Outputs for evaluating the different tissue dissociation methods tested included assessing (a) the percentage of viable (live) cells in the dissociated sample as a proportion of the total cell output, and (b) the total number of viable cells in the dissociated sample per mg of input tissue. Both measurements were determined using a commercially available Beckman Coulter Vi-Cell cell analyzer (a trypan blue dye exclusion-based assay).

TABLE 1

Standard Protocol (Enzyme + Manual Mince)

I. Extraction:
   1. Mice are injected i.p. with 50/5 mg/kg of ketamine/xylazine cocktail.
   2. Once sufficiently sedated, organs are removed for subsequent dissociation.
   3. The hepatic artery is clipped to ensure euthanization.
   4. All extracted tissues are weighed and sub-divided as needed.
II. Place tissues in 5 ml chilled preservation solution DPBS.
III. Mince using scissors until all pieces are ~1-3 mm$^3$.
IV. Incubate in Collagenase IV (1500 u/ml)/(DNase I (2500 u/ml) dissociation buffer at 37 C. using a water bath for 30 minutes, agitating every 5-10 minutes.
V. Top off Dissociation Buffer with 40 ml of RPMI 1640.
VI. Centrifuge dissociated tissue at 300x g for 5 m at RT in a 50 ml centrifuge tube. Upon pelleting, a thick RBC band will be detected in all samples, usually more apparent in CRC samples.
VII. Resuspend the pellet in 1 ml DPBS using a wide-orifice 1 m pipette tip, then add 5 ml of ACK Buffer, swirl the mixture, and then allow to incubate at RT for 5-7 m. Add 45 ml 1% BSA/DPBS (no Ca+/Mg+) as a stop-reaction and pellet the suspension at 300x g for 5 m at RT.
VIII. Resuspend in 10 ml DPBS. Filler through a 70 um sieve or filter, and then top off filtrate with enough DPBS to bring volume up to 10 ml. If digesting a larger piece of tumor, higher volumes may be needed for effective filtering and to keep the cell concentration in range of the ViCell. Change sieves or filters as needed.
IX. Mix and Transfer 600 ul of cell suspension to ViCell tube.
X. Record number and viability using ViCell Program TD
   1. 50 images
   2. 1 aspirate cycle
   3. 3 trypan mix
   4. 5 um-70 um size range
   5. Cell brightness: 85
   6. Cell sharpness: 100
   7. Viable cell brightness: 65
   8. Viable cell spot area: 5
   9. Minimum circularity: 0
   10. Decluster: Med We conducted initial experiments to optimize certain parameters of the LabRAM I system for tissue dissociation, including the following:
1. Exposure Time: the length of time the tissue is exposed to the shear forces.
2. Intensity: the LabRAM I can be tuned to deliver up to 100 g of acceleration to the mixing vessel.
3. Vessel Geometry: the size and shape of the vessel containing the sample can affect shear forces.
4. Vessel Fill Volume: the ratio of liquid buffer vs. dead space in the mixing vessel also affects shear forces.
5. Enzyme/Mincing: some conditions were tested with and without the presence of the enzyme cocktail from Step IV and/or mincing of the tissue in Step III in the Standard Protocol (Table 1).

Example 2

Tissue disruption protocols were performed on mouse liver and kidney tissues as set forth in Table 2 below.

TABLE 2

Sample Conditions Example 2

| Sample No. | Organ Type | Protocol Parameters RAM | Enzyme | Mincing |
|---|---|---|---|---|
| K1 | Kidney | None (Standard protocol) | Yes | Yes |
| K2 | Kidney | Hi | Yes | No |
| K3 | Kidney | Hi | No | No |
| K4 | Kidney | Lo | No | No |
| K5 | Kidney | Hi | Yes | Yes |
| K6 | Kidney | Lo | Yes | Yes |
| K7 | Kidney | Hi | No | Yes |
| K8 | Kidney | Lo | No | Yes |
| L1 | Liver | None (Standard protocol) | Yes | Yes |
| L2 | Liver | Hi | Yes | No |
| L3 | Liver | Hi | No | No |
| L4 | Liver | Lo | No | No |
| L5 | Liver | Hi | Yes | Yes |
| L6 | Liver | Lo | Yes | Yes |
| L7 | Liver | Hi | No | Yes |
| L8 | Liver | Lo | No | Yes |

LabRAM I exposure of the tissue samples came after enzyme or PBS (for "No Enzyme" conditions) incubation and prior to initial centrifugation step (Step VI). Conditions labeled "No Mince" skipped the scissor mincing (Step 111).

Hi Ram conditions are as follows: 1 minute exposure to LabRAM I at 90% intensity (100-110 g of acceleration) in an inverted 50 ml conical tube with 50 ml of PBS.

Lo Ram conditions are as follows: 1 minute exposure to LabRAM I at 50% intensity (62-70 g of acceleration) in an inverted 50 ml conical tube with 50 ml of PBS.

Figure 2:
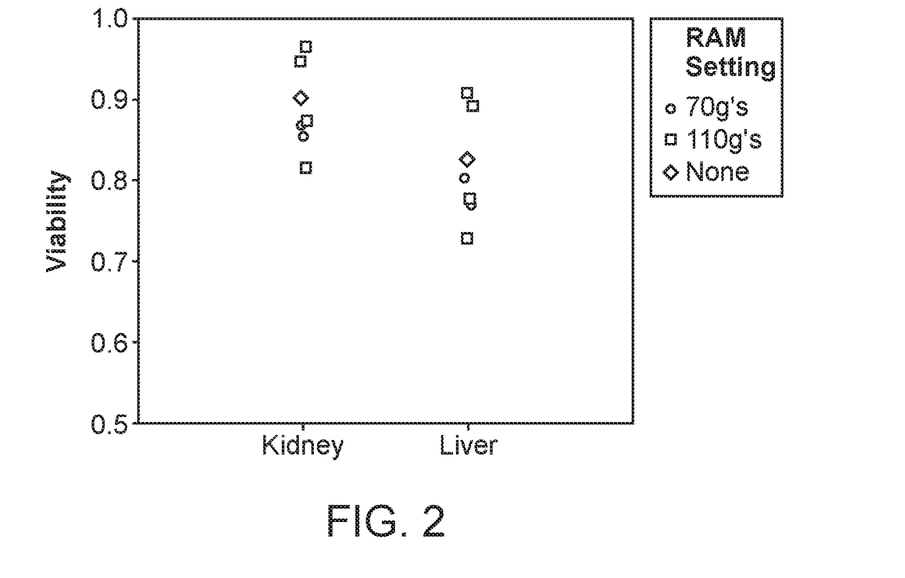
FIG. 2 is a graph showing the viability (Y-axis) of kidney and liver tissue (X-axis) subjected to low intensity (black circles) vs. high intensity (red squares) LabRAM I protocols (see Example 2). Green diamonds represent Standard Protocol from Table 1 (positive control).

FIG. 2 shows the viability (as a percentage) of kidney and liver tissue subjected to low intensity (black circles) vs. high intensity (red squares) LabRAM I protocols. Green diamonds represent cells dissociated using the Standard Protocol (K1 and L1 samples, positive controls). This graph does not differentiate between mincing and enzyme treatment and is intended to simply show that the cells can sufficiently survive the physical rigors of the LabRAM I treatment.

Figure 3:
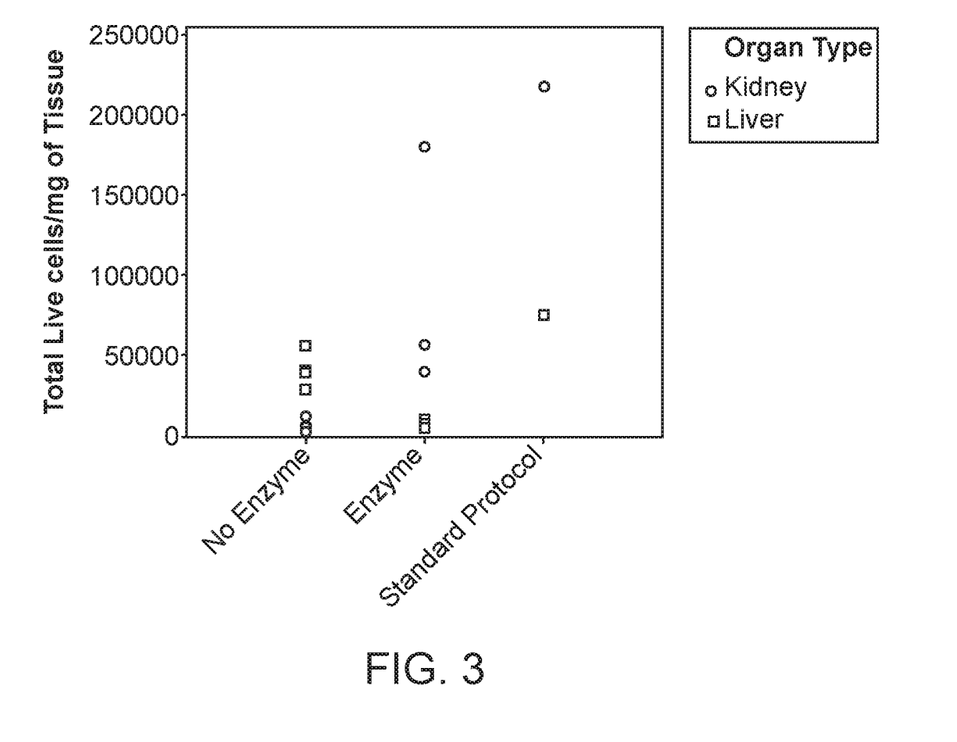
FIG. 3 is a graph showing total viable cells per milligram of input tissue (Y-axis) processed as described in Example 2 with the data separated with respect to enzyme treatment (X-axis). The "no enzyme" and "enzyme" samples were processed by the LabRAM I acoustic mixer while the Standard Protocol was not. Kidney samples are shown in black circles and liver samples are shown in red squares.

FIG. 3 shows the total viable (or "Live") cells per milligram of input tissue and separates the samples with respect to enzyme treatment (no enzyme vs. enzyme vs. standard protocol). Kidney samples are shown in black circles and liver samples are shown in red squares. This Figure shows that enzyme treatment was important in retrieving a sufficient number of viable cells from kidney tissue, but was deleterious to obtaining the more fragile liver cells.

Example 3

Tissue disruption protocols were performed on mouse liver and kidney tissues as set forth in Table 3 below.

TABLE 3

Sample Conditions Example 3

| Sample No. | Organ Type | Protocol Parameters | | | |
|---|---|---|---|---|---|
| | | RAM | Enzyme | Mincing | Fill (%) |
| K1 | Kidney | None (Standard protocol) | Yes | Yes | N/A |
| K2 | Kidney | Hi | Long | Yes | No | 100 |
| K3 | Kidney | Hi | Long | Yes | No | 50 |
| K4 | Kidney | Hi | Short | Yes | No | 100 |
| K5 | Kidney | Hi | Short | Yes | No | 50 |
| K6 | Kidney | Lo | Long | Yes | No | 100 |
| K7 | Kidney | Lo | Long | Yes | No | 50 |
| K8 | Kidney | Lo | Short | Yes | No | 100 |
| K9 | Kidney | Lo | Short | Yes | No | 50 |
| K10 | Kidney | Hi | Long | No | Yes | 100 |
| K11 | Kidney | Hi | Long | No | Yes | 50 |
| K12 | Kidney | Lo | Long | No | Yes | 100 |
| K13 | Kidney | Lo | Long | No | Yes | 50 |
| K14 | Kidney | Lo | Long | Yes | Yes | 100 |
| K15 | Kidney | Lo | Long | Yes | Yes | 50 |
| K16 | Kidney | Hi | Long | Yes | Yes | 100 |
| L1 | Liver | None (Standard protocol) | Yes | Yes | N/A |
| L2 | Liver | Hi | Long | No | No | 100 |
| L3 | Liver | Hi | Long | No | No | 50 |
| L4 | Liver | Hi | Short | No | No | 100 |
| L5 | Liver | Hi | Short | No | No | 50 |
| L6 | Liver | Lo | Long | No | No | 100 |
| L7 | Liver | Lo | Long | No | No | 50 |
| L8 | Liver | Lo | Short | No | No | 100 |
| L9 | Liver | Lo | Short | No | No | 50 |
| L10 | Liver | Hi | Long | No | Yes | 100 |
| L11 | Liver | Hi | Long | No | Yes | 50 |
| L12 | Liver | Lo | Long | No | Yes | 100 |
| L13 | Liver | Lo | Long | No | Yes | 50 |
| L14 | Liver | Lo | Long | Yes | Yes | 100 |
| L15 | Liver | Lo | Long | Yes | Yes | 50 |
| L16 | Liver | Hi | Long | Yes | Yes | 100 |

Based on the results shown in Study 1 and shown in FIG. 3 (described above), the majority of kidney samples tested in this study underwent the enzyme treatment step while the majority of liver samples were not treated with enzyme.

In these experiments, the mixing vessel was changed from a 50 ml conical tube to a 15 ml conical tube to increase shear forces. The vessels were either filled to 7.5 ml (50% Fill) or 15 ml (100% Fill) of media (PBS) during LabRAM I exposure.

Short LabRAM I exposure is 1 minute while Long LabRAM I exposure is 3 minutes.

Hi LabRAM I exposure is 90% intensity (100-110 g of acceleration) and Lo LabRAM I exposure is 50% intensity (62-70 g of acceleration).

Figure 4:
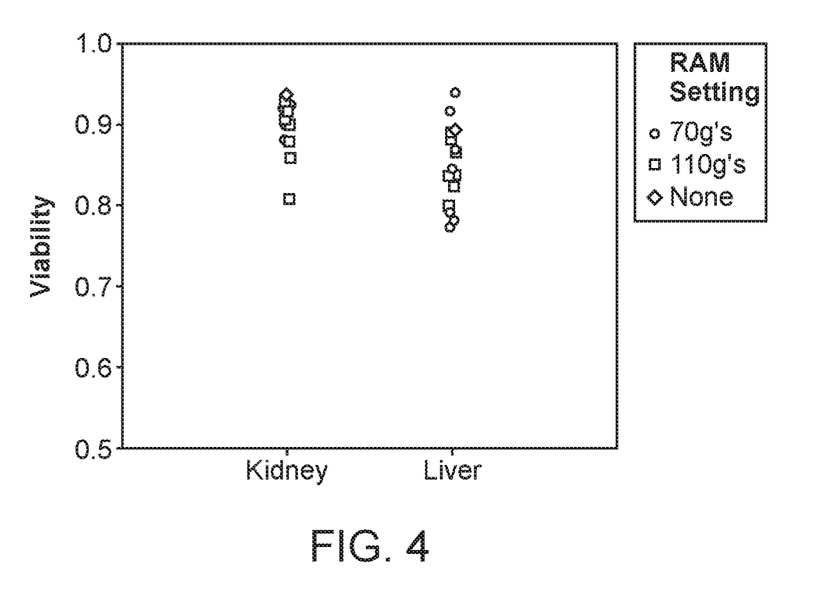
FIG. 4 is a graph showing the viability (Y-axis) of kidney and liver tissue subjected to low intensity (black circles) vs. high intensity (red squares) LabRAM I protocols in Example 3. Green diamonds represent Standard Protocol from Table 1 (positive control). This graph does not differentiate with respect to the mincing and enzyme treatment.

FIG. 4 shows the viability of kidney and liver tissue subjected to low intensity (black circles) vs. high intensity (red squares) LabRAM I protocols. The Green diamonds represent tissue dissociated using the Standard Protocol from Table 1 (K1 and L1 samples, positive controls). This graph does not differentiate between mincing and enzyme treatment and is intended to simply show that these cells can sufficiently survive the physical rigors of the LabRAM I treatment.

Figure 5:
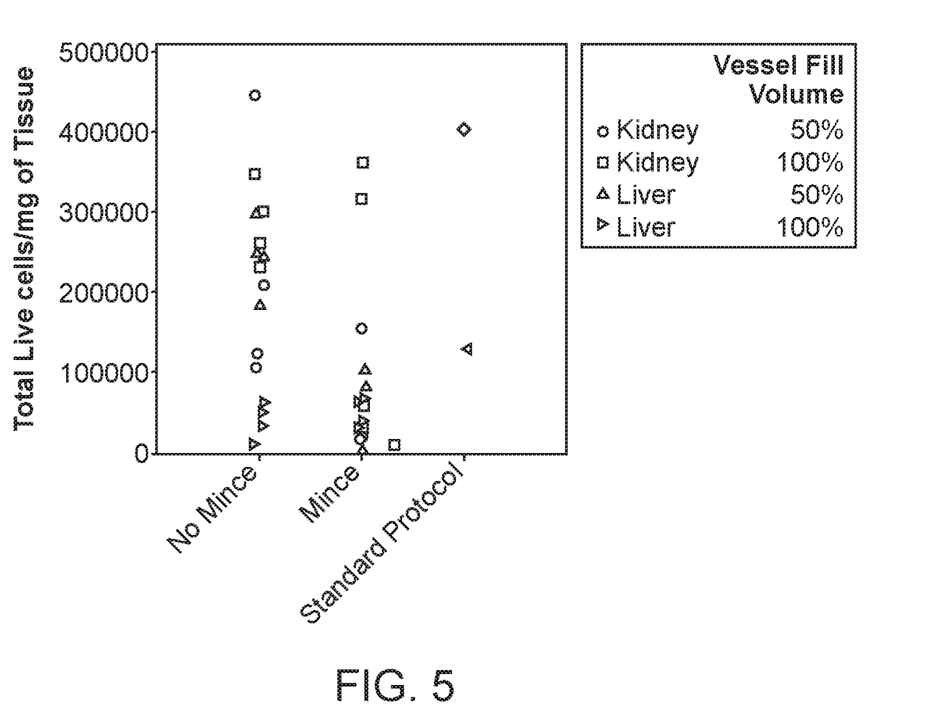
FIG. 5 is a graph showing total viable cells per milligram of input tissue (Y-axis) comparing LabRAM I protocols in Example 3 with respect to mincing (with and without) as well as the vessel fill volume. Results using the Standard Protocol are also shown.

FIG. 5 shows total viable cells per milligram of input tissue and separates the samples based on mincing (on X axis) and vessel fill volume (see legend in FIG. 5). These data show that liver tissue (shown in triangles) are dissociated most efficiently without manual pre-mincing and using 50% vessel fill volume (compare upward pointing traingles to those pointing rightward). No significant difference in dissociation of kidney tissue was seen between mincing/no mincing samples and between 100% fill and 50% fill samples.

Example 4

Tissue disruption protocols were performed on mouse liver and kidney tissues as set forth in Table 2 below.

TABLE 4

Sample Conditions Example 4

| Sample No. | Organ Type | Protocol Parameters | | | |
|---|---|---|---|---|---|
| | | RAM | Enzyme | Mincing | Fill (%) |
| K1 | Kidney | None (Standard protocol) | Yes | Yes | N/A |
| K2 | Kidney | None (Standard protocol) | No | No | N/A |
| K3 | Kidney | Hi | Long | Yes | No | 100 |
| K4 | Kidney | Lo | Long | Yes | No | 100 |
| K5 | Kidney | Lo | Long | Yes | No | 50 |
| K6 | Kidney | Lo | Long | Yes | No | 100 |
| K7 | Kidney | Lo | Long | Yes | No | 50 |
| K8 | Kidney | Lo | Long | Yes | Yes | 100 |
| K9 | Kidney | Lo | Long | Yes | Yes | 50 |
| K10 | Kidney | Hi | Long | Yes | Yes | 100 |
| K11 | Kidney | Hi | Longer | Yes | No | 100 |
| K12 | Kidney | Lo | Longer | Yes | No | 100 |
| K13 | Kidney | Lo | Longer | Yes | No | 50 |
| K14 | Kidney | Lo | Longer | Yes | Yes | 100 |
| K15 | Kidney | Lo | Longer | Yes | Yes | 50 |
| K16 | Kidney | Hi | Longer | Yes | Yes | 100 |
| L1 | Liver | None (Standard protocol) | Yes | Yes | N/A |
| L2 | Liver | None (Standard protocol) | Yes (50%) | Yes | N/A |
| L3 | Liver | None | No | No | N/A |
| L4 | Liver | Hi | Long | No | Yes | 100 |
| L5 | Liver | Hi | Long | No | No | 50 |
| L6 | Liver | Hi | Long | No | Yes | 50 |
| L7 | Liver | Hi | Short | No | No | 50 |
| L8 | Liver | Hi | Short | No | Yes | 50 |
| L9 | Liver | Lo | Long | No | No | 50 |
| L10 | Liver | Lo | Long | No | Yes | 50 |
| L11 | Liver | Lo | Short | No | No | 50 |
| L12 | Liver | Lo | Short | No | Yes | 50 |
| L13 | Liver | Hi | Long | No | No | 50 |
| L14 | Liver | Hi | Short | No | No | 50 |
| L15 | Liver | Lo | Long | No | No | 50 |
| L16 | Liver | Lo | Short | No | No | 50 |

In these experiments, all kidney samples included an enzyme treatment step while all liver samples skipped the enzyme treatment step. In addition, all but 4 liver samples skipped mincing step as well. (These experimental design choices were based on results described above.)

Vessels used were 15 ml conicals and were filled to either 7.5 ml (50%) or 15 ml (100%) (all but 1 of the liver samples were filled to 7.5 ml based on experiments above).

Short LabRAM I exposure is 1 minute, Long LabRAM I exposure is 3 minutes, and Longer LabRAM I exposure is 5 minutes. This longer exposure was only tested in kidney samples as it was deemed unnecessary for liver tissue. HI and Lo LabRAM I exposure is as described in Example 3.

Figure 6:
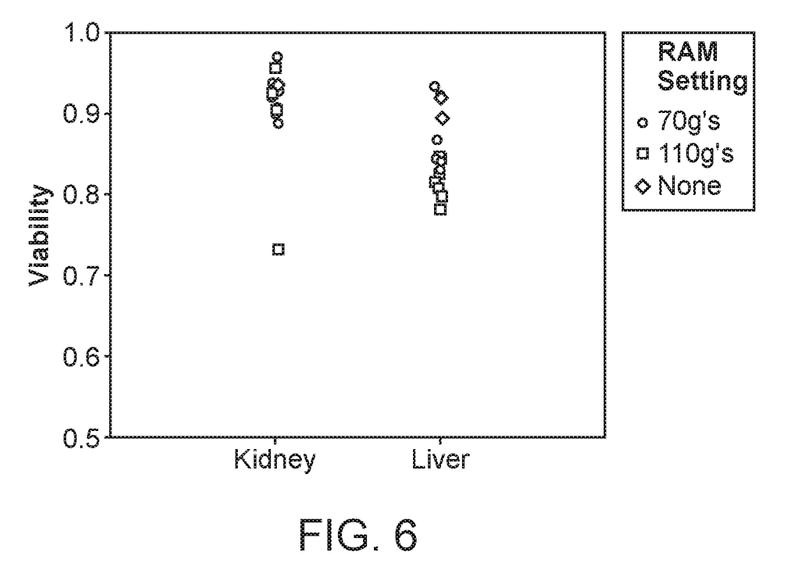
FIG. 6 is a graph showing the viability (Y-axis) of kidney and liver tissue (X-axis) subjected to the low intensity (black circles) vs. high intensity (red squares) LabRAM I protocols in Example 4. Green diamonds represent Standard Protocol from Table I. This graph does not differentiate mincing and enzyme treatment.

FIG. 6 shows the viability of kidney and liver tissue subjected to low intensity (black circles) vs. high intensity (red squares) LabRAM I protocols. Green diamonds represent tissue dissociated using the Standard Protocol from Table 1 (K1, K2, L1 and L2 samples, positive controls)(Note that one control sample for each tissue was dissociated using 50% of the enzyme dose). This graph does not differentiate between mincing and enzyme treatment and is intended to simply show that these cells can sufficiently survive the physical rigors of the LabRAM I treatment.

Figure 7:
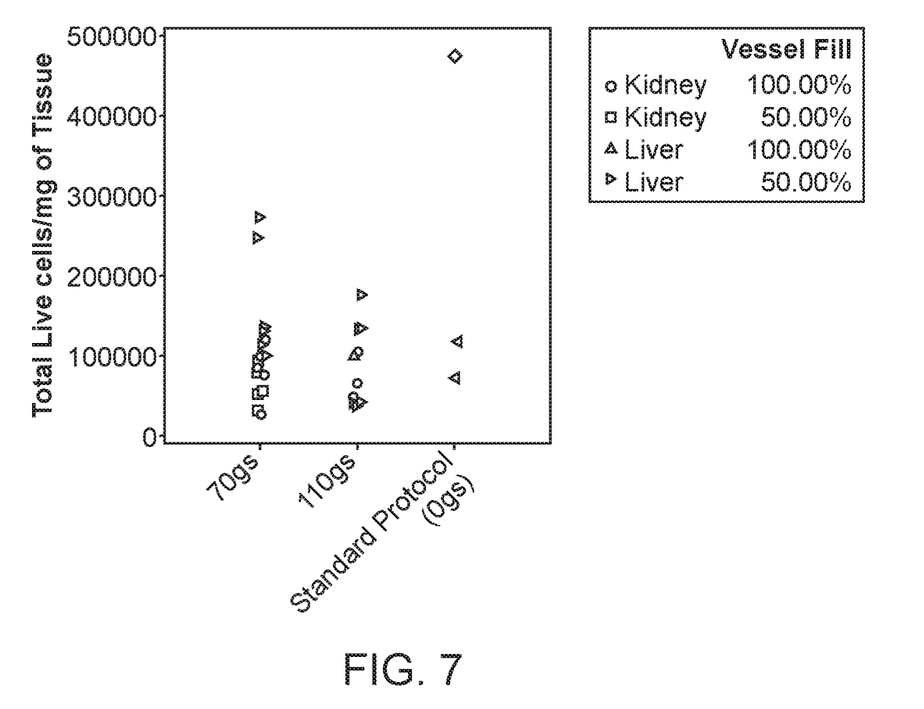
FIG. 7 is a graph showing total viable cells per milligram of input tissue (Y-axis) comparing LabRAM I protocols in Example 4 with respect to vessel fill volume and intensity of LabRAM I treatment (see legend in FIG. 7). Total viable cells from the Standard Protocol processing of liver (left-pointing triangles) and kidney (green diamond) are also shown.

FIG. 7 shows total viable cells per milligram of input tissue and separates the data based on vessel fill volume (see legend) and intensity of LabRAM I treatment (X axis). These data show that liver tissue can be dissociated using only LabRAM I treatment while achieving equivalent viability and better cell yields than current standard protocols that are laborious and expensive (compare right-pointing triangles and left-pointing triangles). While viable kidney cells could be obtained in significant numbers from the LabRAM I protocol, these protocols did not dissociate kidney tissue as well as the standard protocol. Regardless, it is clear from the data that sufficient live cells can be obtained from the LAbRAM I protocol to dissociate kidney tissue.

Figure 8:
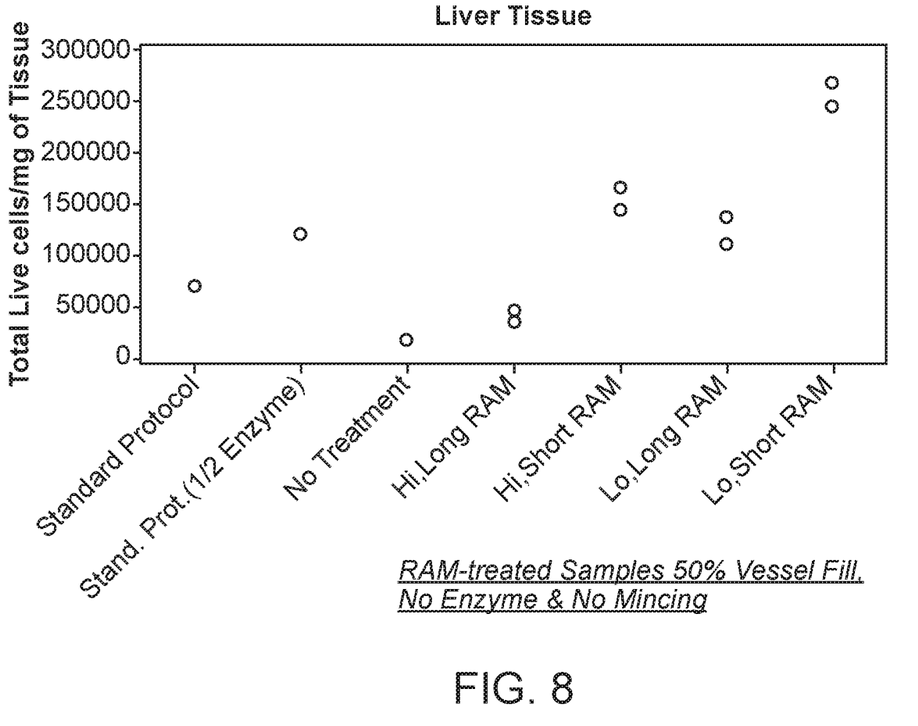
FIG. 8 is a graph showing total viable cells per milligram of liver tissue (Y-axis) under different Standard and LabRAM I protocols (X-axis) as described in Example 4. The last four protocols were performed in duplicate. This graph shows clear and reproducible evidence that acoustic energy-based mixing can be used to dissociate liver tissue more thoroughly than the standard protocol.

FIG. 8 shows total viable cells per milligram of liver tissue dissociated with 50% fill (i.e., 7.5 mL in a 15 mL conical), no enzyme treatment, and no mincing. The data is separated based on the different LabRAM I protocols (X-axis). Some protocols were run in duplicate (last 4 LabRAM I protocols in the graph, which have two replicate experiments). From these data it is clear that for liver tissue disruption, Short LabRAM I exposure (1 min.) is better that Long LabRAM I exposure (3 min.), and Lo LabRAM I intensity (50%; 62-70 g of acceleration) is better than Hi LabAM I intensity (90%; 100-110 g of acceleration).

The data provided herein clearly shows that the LabRAM I system can be used to dissociate liver tissue more thoroughly and efficiently than the Standard protocol.

Discussion

The Standard Protocol employed in the experiments described above (which is representative of protocols currently used in the art) employs two key steps: manual mincing (e.g., using razors, scissors, mortar and pestle, etc.) and enzyme treatment (e.g., collagenase). Such protocols require a researcher to cut the sample into small pieces, the size and geometry of which is highly variable depending on the chosen method and the individual researcher performing the task. The enzyme treatment requires expensive enzymes or enzyme cocktails as well as moderate to long incubation times. In addition, such protocols require a heated water bath or other heating element to maintain the elevated temperature needed to ensure optimal enzymatic activity throughout the incubation. An instrument or method of thoroughly dissociating solid tumors into viable single-cell suspensions without the subjectivity of manual mincing and/or the need for expensive enzymes and/or time-consuming workflows would be highly desirable.

The results provided above show that the low frequency, high intensity acoustic energy, e.g., provided by the LabRAM I instrument, can be employed to dissociate tissue into a single cell suspension containing sufficient numbers of viable cells for analysis and/or downstream assays.

For example, the LabRAM I was shown to be effective at dissociating liver tissue into a highly viable single-cell suspension in 1 minute without the need for manual mincing or enzyme treatment. While the acoustic energy methods tested on kidney tissue described above did not return as high a percentage of viable kidney cells in suspension as the Standard Protocol (calculated as viable cells/mg of input tissue), sufficient numbers of cells were obtained from kidney samples for downstream processing.

EMBODIMENTS

Aspects of the present disclosure include a method of producing a cellular suspension from a tissue sample, the method comprising: applying resonant acoustic energy to a container comprising the tissue sample in a manner sufficient to produce a cellular suspension from the tissue sample. In certain embodiments, the resonant acoustic energy has a frequency ranging from 10 to 100 Hz. In any preceding embodiment, the container is a sealed container. In any preceding embodiment, the container has a volume ranging from 10 to 500 ml. In any preceding embodiment, the tissue sample is a mammalian tissue sample. In certain embodiments, the tissue sample is a biopsy sample, e.g., a tumor biopsy sample. In any preceding embodiment, the method further comprises manipulating the cellular suspension. In certain embodiments, the manipulating comprises flow cytometrically processing the cellular suspension, e.g., analyzing and/or sorting the cellular suspension. In any preceding embodiment, the method further comprises assaying a cell of the cellular suspension. In certain embodiments, the assaying comprises nucleic acid analysis, e.g., nucleic acid sequencing, expression level detection, and the like. In any preceding embodiment, the method comprises obtaining the tissue sample. In any preceding embodiment, the container further comprises an enzymatic dissolution agent. In any preceding embodiment, the container further comprises a milling agent. In certain embodiments, the method further comprises separating the milling agent from the cellular suspension.

Aspects of the present disclosure include a resonant acoustic mixer comprising: a mixing container; a resonant acoustic energy source operatively coupled to the mixing container; and a tissue sample present in the mixing container. In certain embodiments, the resonant acoustic energy source is configured to apply acoustic energy having a frequency ranging from 10 to 100 Hz to the mixing container. In any preceding embodiment, the mixing container is a sealed container. In any preceding embodiment, the container has a volume ranging from 10 to 500 ml. In any preceding embodiment, the tissue sample is a mammalian tissue sample. In certain embodiments, the tissue sample is a biopsy sample, e.g., a tumor biopsy sample. In any preceding embodiment, the resonant acoustic mixer is operatively coupled to a flow cytometer. In certain embodiments, the flow cytometer is a cell sorter. In any preceding embodiment, the container further comprises an enzymatic dissolution agent. In any preceding embodiment, the container further comprises a milling agent.

Aspects of the present disclosure include a kit for use in producing a cellular suspension from a tissue sample, the kit comprising: an enzymatic dissolution agent; and a milling agent.

Notwithstanding the appended clauses, the disclosure set forth herein is also defined by the following clauses:

1. A method of producing a cellular suspension from a tissue sample, the method comprising:
   applying resonant acoustic energy to a container comprising the tissue sample in a manner sufficient to produce a cellular suspension from the tissue sample.
2. The method according to Clause 1, wherein the resonant acoustic energy has a frequency ranging from 10 to 100 Hz.
3. The method according to Clause 1 or 2, wherein the container is a sealed container.
4. The method according to any of Clauses 1 to 3, wherein the container has a volume ranging from 10 to 500 ml.
5. The method according to any of Clauses 1 to 4, wherein the tissue sample is a mammalian tissue sample.
6. The method according to Clause 5, wherein the tissue sample is a biopsy sample.
7. The method according to Clause 6, wherein the biopsy sample is a tumor biopsy sample.
8. The method according to any of the preceding clauses, wherein the method further comprises manipulating the cellular suspension.
9. The method according to Clause 8, wherein the manipulating comprises flow cytometrically processing the cellular suspension.
10. The method according to Clause 9, wherein the flow cytometrically processing the cellular suspension comprises sorting the cellular suspension.
11. The method according to any of the preceding clauses, wherein the method further comprises assaying a cell of the cellular suspension.
12. The method according to Clause 11, where the assaying comprises nucleic acid analysis.
13. The method according to Clause 12, wherein the nucleic acid analysis comprises nucleic acid sequencing.
14. The method according to Clause 12 or 13, wherein the nucleic acid analysis comprises expression level detection.
15. The method according to any of the preceding clauses, wherein the method comprises obtaining the tissue sample.
16. The method according to any of the preceding clauses, wherein the container further comprises an enzymatic dissolution agent.
17. The method according to any of the preceding clauses, wherein the container further comprises a milling agent.
18. The method according to Clause 17, wherein the method further comprises separating the milling agent from the cellular suspension.
19. A resonant acoustic mixer comprising:
   a mixing container;
   an resonant acoustic energy source operatively coupled to the mixing container; and
   a tissue sample present in the mixing container.
20. The resonant acoustic mixer according to Clause 19, wherein the resonant acoustic energy source is configured to apply acoustic energy having a frequency ranging from 10 to 100 Hz to the mixing container.
21. The resonant acoustic mixer according to Clause 19 or 20, wherein the mixing container is a sealed container.
22. The resonant acoustic mixer according to any of Clauses 19 to 21, wherein the container has a volume ranging from 10 to 500 ml.
23. The resonant acoustic mixer according to any of Clauses 19 to 22, wherein the tissue sample is a mammalian tissue sample.
24. The resonant acoustic mixer according to Clause 23, wherein the tissue sample is a biopsy sample.
25. The resonant acoustic mixer according to Clause 24, wherein the biopsy sample is a tumor biopsy sample.
26. The resonant acoustic mixer according to any of Clauses 19 to 25, wherein the resonant acoustic mixer is operatively coupled to a flow cytometer.
27. The resonant acoustic mixer according to Clause 26, wherein the flow cytometer is a cell sorter.
28. The resonant acoustic mixer according to any of Clauses 19 to 27, wherein the container further comprises an enzymatic dissolution agent.
29. The resonant acoustic mixer according to any of Clauses 19 to 28, wherein the container further comprises a milling agent.
30. A kit for use in producing a cellular suspension from a tissue sample, the kit comprising:
   an enzymatic dissolution agent; and
   a milling agent.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a cellular suspension from a tissue sample, the method comprising:
   applying resonant acoustic energy to a container comprising the tissue sample at a frequency ranging from 20 Hz to 20,000 Hz to dissociate cells from the tissue sample and produce live dissociated cells in a cellular suspension from the tissue sample.
2. The method according to claim 1, wherein the container is a sealed container.
3. The method according to claim 1, wherein the tissue sample is a mammalian tissue sample.
4. The method according to claim 3, wherein the tissue sample is a biopsy sample.
5. The method according to claim 4, wherein the biopsy sample is a tumor biopsy sample.
6. The method according to claim 1, wherein the method further comprises manipulating the cellular suspension.
7. The method according to claim 6, wherein the manipulating comprises flow cytometrically processing the cellular suspension.

8. The method according to claim 7, wherein the flow cytometrically processing the cellular suspension comprises sorting the cellular suspension.

9. The method according to claim 1, wherein the method further comprises assaying a cell of the cellular suspension.

10. The method according to claim 9, where the assaying comprises nucleic acid analysis.

11. The method according to claim 1, wherein the container further comprises at least one of an enzymatic dissolution agent and a milling agent.

12. The method according to claim 1, wherein the resonant acoustic energy is supplied by cyclic linear displacement of the container.

* * * * *